United States Patent
Griffiths-Brophy et al.

(10) Patent No.: US 8,163,298 B2
(45) Date of Patent: Apr. 24, 2012

(54) AQUEOUS GEL HAVING AN ALPHA-HYDROXY ACID AND SUSPENDED PARTICULATES

(75) Inventors: Susan Adair Griffiths-Brophy, Middletown, OH (US); Dennis Eugene Kuhlman, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 374 days.

(21) Appl. No.: 12/607,553

(22) Filed: Oct. 28, 2009

(65) Prior Publication Data

US 2010/0119619 A1 May 13, 2010

Related U.S. Application Data

(60) Provisional application No. 61/109,354, filed on Oct. 29, 2008.

(51) Int. Cl.
*A61K 9/00* (2006.01)
*A61K 8/02* (2006.01)
*A61K 33/26* (2006.01)
*A61K 33/24* (2006.01)
*A61K 8/00* (2006.01)
*A61K 8/18* (2006.01)
*A61K 31/715* (2006.01)
*A61K 47/00* (2006.01)
*C08L 1/00* (2006.01)

(52) U.S. Cl. ........ 424/400; 424/401; 424/646; 424/617; 424/62; 424/63; 514/57; 514/848; 514/844; 514/772.2; 106/162.9

(58) Field of Classification Search .................. 424/400
See application file for complete search history.

(56) References Cited

U.S. PATENT DOCUMENTS

| | | | |
|---|---|---|---|
| 5,013,473 A | 5/1991 | Norbury et al. | |
| 5,849,314 A | 12/1998 | Dobkowski | |
| 6,007,264 A | 12/1999 | Koptis | |
| 6,258,345 B1 | 7/2001 | Rouquet | |
| 6,342,237 B1 | 1/2002 | Bara | |
| 6,696,049 B2 | 2/2004 | Vatter | |
| 6,902,335 B2 | 6/2005 | Bergey | |
| 2003/0021817 A1* | 1/2003 | Arnaud-Sebillotte et al. | .. 424/63 |
| 2003/0113356 A1 | 6/2003 | Deckner et al. | |
| 2004/0022823 A1 | 2/2004 | Uchida et al. | |
| 2004/0028711 A1 | 2/2004 | Uchida et al. | |
| 2004/0175347 A1 | 9/2004 | Bissett | |
| 2006/0083761 A1 | 4/2006 | Yoshimi et al. | |
| 2006/0099026 A1 | 5/2006 | Griffin | |
| 2006/0134156 A1 | 6/2006 | Marion | |
| 2006/0275237 A1 | 12/2006 | Bissett et al. | |
| 2007/0025938 A1 | 2/2007 | Hansenne | |
| 2007/0025947 A1 | 2/2007 | Hansenne | |
| 2007/0025949 A1 | 2/2007 | Hansenne | |
| 2007/0031355 A1 | 2/2007 | Fonolla | |
| 2007/0196403 A1 | 8/2007 | Uchida et al. | |
| 2008/0181956 A1 | 7/2008 | Ha et al. | |
| 2009/0017080 A1 | 1/2009 | Tanner et al. | |
| 2010/0092408 A1 | 4/2010 | Breyfogle et al. | |

FOREIGN PATENT DOCUMENTS

| | | |
|---|---|---|
| EP | 27730 A2 | 10/1981 |
| EP | 586929 B1 | 3/1994 |
| EP | 627215 B1 | 5/1998 |
| EP | 1259220 | 11/2002 |
| WO | WO 0038621 | 7/2000 |

* cited by examiner

*Primary Examiner* — Brian-Yong Kwon
*Assistant Examiner* — Terry Cohen
(74) *Attorney, Agent, or Firm* — S. Robert Chuey; Eric T. Addington; James C. Vago

(57) ABSTRACT

A personal care composition in the form of an aqueous gel may comprise an alpha-hydroxy acid, wherein the pH of the composition is less than about 4.5. The personal care composition comprises a gelling agent and an aqueous solvent. The personal care composition further comprises particulates and an effective amount of suspension agent to suspend the particulates. The personal care composition exhibits a consumer desired viscosity and translucency.

5 Claims, No Drawings

AQUEOUS GEL HAVING AN ALPHA-HYDROXY ACID AND SUSPENDED PARTICULATES

CROSS REFERENCE TO RELATED APPLICATION

This application claims the benefit of U.S. Provisional Application Ser. No. 61/109,354, filed Oct. 29, 2008.

FIELD OF THE INVENTION

The present invention relates to a personal care composition in the form of an aqueous gel comprising an alpha-hydroxy acid and suspended particulates. The personal care composition provides consumer desired skin feel attributes while maintaining an acceptable degree of translucency.

BACKGROUND OF THE INVENTION

Aqueous gels offer an ideal platform for delivery of water soluble actives. Aqueous gels provide good absorption benefits and desirable skin feel attributes. Gel compositions also offer a platform from which a visually appealing product can be created. However, creation of a stable and consumer pleasing aqueous gel is difficult at low pH as needed for efficacious delivery of acidic actives. Acidic actives may be used as an exfoliant, a wrinkle reduction agent, pigmentation/tone aid, or as an active to improve many other skin conditions.

Inclusion of acidic actives can adversely impact desired characteristics of an aqueous gel. Maintenance of consumer preferred viscosity is one challenge associated with an acidic gel. Many conventional thickeners quickly degrade in the acidic environment resulting in destabilization and loss of viscosity over time. More robust thickeners often adversely affect the aesthetic properties of the gel. Namely, the gels can cloud, which limits the value of the gels as a platform for visually interesting designs or adjuncts (e.g., platelet particulates, encapsulate particulates, etc.).

One such adjunct known in the personal care arts is platelet particulates. Platelet particulates can provide a pearlescent or nacreous effect or light interference. A particularly effective platelet particulate is a mica platelet coated with thin layers of metal oxides such as $TiO_2$ or $Fe_2O_3$. The thickness of the metal oxide layer(s) can be varied to yield unique color effects. Suspending platelet particulates in an aqueous gel is problematic when coupled with the requirements of maintaining a low pH, suitable viscosity, and an acceptable degree of translucency.

There is a need for an aqueous gel personal care composition comprising an acidic active at a low pH. The aqueous gel should exhibit consumer desirable viscosity. Furthermore, the aqueous gel should maintain consumer desired translucency while allowing for the suspension of aesthetically pleasing particulates.

SUMMARY OF THE INVENTION

The present invention addresses the needs identified in the Background. In one embodiment, a personal care composition is in the form of an aqueous gel comprising about 0.1% to about 7.0% of an alpha-hydroxy acid, wherein the pH of the composition is less than about 4.5. The personal care composition comprises a gelling agent and about 60% to about 95% of an aqueous solvent. The personal care composition further comprises an effective amount of particulates and an effective amount of suspension agent to suspend the particulates. The composition has a viscosity from about 10,000 cps to about 50,000 cps and exhibits a turbidity of less than 900 NTU.

In another embodiment, the personal care composition in the form of an aqueous gel comprising about 0.1% to about 7.0% of glycolic acid, wherein the pH of the composition is less than about 4.5. The personal care composition comprises about 0.1% to about 3% of a gelling agent, wherein said gelling agent is a modified cellulose, and about 60% to about 95% of an aqueous solvent. The personal care composition further comprises from 0.0001% to about 0.3% of platelet particulates and at least about 0.01% of a suspension agent to suspend the platelet particulates, wherein the suspension agent is selected from a group consisting of xanthan gum, microfibrous cellulose, and mixtures thereof. The composition has a viscosity from about 10,000 cps to about 50,000 cps and exhibits a turbidity of less than 900 NTU.

The present invention also relates to a method of exfoliating the skin. The method comprises the steps of applying a personal care composition as described herein to the skin of a user prior to a primary sleep event, leaving the personal care composition on during the primary sleep event, and removing the personal care composition after the end of the primary sleep event.

In another embodiment, the present invention relates to a method of marketing a personal care composition for chemical exfoliation of skin. The method comprises the steps of providing the personal care composition as described herein, providing instruction to a user to apply the composition prior to a primary sleep event of the user, and providing instruction to the user to remove the personal care composition at the end of the primary sleep cycle.

DETAILED DESCRIPTION OF THE INVENTION

All ratios are weight ratios, unless specifically stated otherwise. All ranges are inclusive and combinable; therefore, every range given throughout this specification will include every narrower range that falls within such broader range as if such narrower ranges were all expressly written herein. The number of significant digits conveys neither a limitation on the indicated amounts nor on the accuracy of the measurements. All measurements are understood to be made at ambient conditions. All such weights as they pertain to listed ingredients are based on the active level and do not include carriers or by-products that may be included in commercially available materials, unless otherwise specified.

The personal care compositions of the present invention comprise an acidic active. The acidic active may be a hydroxy acid such as an alpha- or beta-hydroxy acid. In particular embodiments, the acidic active is an alpha-hydroxy acid selected from glycolic acid, lactic acid, malic acid, citric acid, and mixtures thereof. In certain embodiments, glycolic acid is preferred for its skin peel and exfoliation benefits.

The personal care composition may comprise about 0.1% to about 7.0% of the acidic active. Particularly with alpha-hydroxy acids, exceeding 7.0% often results in undesirable irritation to users of the personal care composition. In other embodiments, the personal care composition may comprise greater than about 1% to about 2% of the acidic active. The personal care composition may comprise less than 4% to about 5% of the acidic active.

The efficacy of the acidic active may correlate to the pH of the personal care composition. A lower composition pH yields increased bioavailability of the acidic active. This is particularly seen with alpha-hydroxy acids such as glycolic acid. The personal care composition of the present invention typically exhibits a pH of less than about 4.5 in order to maintain the efficacy of the acid active. A suitable pH range is from about 3.5 to about 4.5 or, alternately, from about 3.8 to about 4.2. Acidity may be regulated by adjusting the amount of alkaline neutralizing ingredients in the personal care composition. Suitable neutralizing ingredients include triethanolamine, potassium hydroxide, ammonium hydroxide, sodium hydroxide, and alkaline compounds listed as "pH Adjusters" in The Cosmetic, Toiletry, and Fragrance Association's (CTFA) *The International Cosmetic Ingredient Dictionary and Handbook*, 10$^{th}$ Ed., Gottschalck, T. E. and McEwen, Jr., Eds. (2004). Neutralizing agents may be used in a quantity to achieve the desired compositional pH. In one embodiment, the personal care composition comprises about 1% to about 5% of neutralizing agents. In a particular embodiment, the personal care composition comprises from about 1% to about 2% triethanolamine and from about 2% to about 3% of sodium hydroxide.

Formation of a low pH personal care composition while providing other consumer preferred attributes is unappreciated in the prior art. Consumers desire a gel composition for its unique skin feel and absorption benefits. Consumers desire a suitably viscous composition. Consumers also desire a gel composition that has unique aesthetic properties such as substantial translucency and the ability to deliver particulate material. Delivering these consumer preferred characteristics while maintaining the pH of the composition (and, thereby, the efficacy of the acidic active) is a goal of the present personal care composition.

The personal care composition may be in the form of an aqueous gel. Gel systems may comprise a gelling agent and a solvent. Typically, for aqueous gels, water is a suitable solvent; however, water may be substituted by or supplemented with other aqueous solvents such as polyols (e.g., glycerin, butylene glycol, pentylene glycol, etc.). The aqueous gel may comprise about 60% to about 95% of the aqueous solvent.

Suitable gelling agents generally may include water-soluble or colloidally water-soluble polymers, which includes synthetic and natural polymers, and to particulate based materials.

Suitable synthetic gelling agents include carboxylic acid copolymers. These copolymers consist essentially of a colloidally water-soluble polymer of acrylic acid crosslinked with a polyalkenyl polyether of a polyhydric alcohol, and optionally an acrylate ester or a polyfunctional vinylidene monomer. Examples of carboxylic acid copolymers useful in the present invention include the Carbopol™ series and the Pemulen™ series from Noveon Consumer Specialties, Inc., Cleveland, Ohio.

Other carboxylic acid copolymers may include sodium salts of acrylic acid/acrylamide copolymers sold by the Hoechst Celanese Corporation under the trademark of Hostaceren PN73. Also included are the hydrogel polymers sold by Lipo Chemicals Inc., Paterson, N.J., under the trademark of HYPAN hydrogels such as HYPAN SA100 H.

Suitable gelling agents may also comprise acrylate or acrylamide copolymers. A suitable acrylate copolymer is Sepinov EMT-10 from Seppic, Fairfield, N.J., which is a hydroxyethyl acrylate/sodium acryloyldimethyl taurate copolymer.

Suitable natural gelling agents may include gelatin, polysaccharides, and mixtures thereof. Exemplary polysaccharides include, but are not limited to, red seaweed polysaccharides, glucomannans, galactomannans such as guar gum, fermentation polysaccharides and derivatives thereof such as xanthan gum, brown seaweed polysaccharides, extracts of marine invertebrates, starch and derivatives thereof, natural fruit extracts, plant fiber derivatives, kelp, natural plant exudates, and resinous gums, cellulose, cellulose ethers (e.g. hydroxyethyl cellulose, methyl cellulose, hydroxy propylmethyl cellulose), and mixtures thereof. Other suitable gelling agents are disclosed in the section entitled "Gelling Agents" in U.S. Patent Application Publication 2003/0113356 A1, published Jun. 19, 2003.

Suitable particulate gelling agents may include finely divided or colloidal silicas, fumed silicas, and silicates, which includes montmorillonite clays and hydrophobically treated montmorillonites (e.g., bentonites, hectorites and colloidal magnesium silicates).

Suitable gelling agents should be pH tolerant such that the consumer preferred viscosity may be maintained. The gelling agent should maintain the viscosity for the normal life span of the personal care product. For example, the viscosity should be maintained for at least about 8 weeks. Many gelling agents are unable to adequately gel in a highly acidic environment. Furthermore, suitable gelling agents should also maintain the consumer preferred transparency of the personal care composition. Preferred gelling agents include hydroxyethyl cellulose and modified and unmodified cellulose materials in general.

An effective amount of the gelling agent may be used to achieve the consumer preferred viscosity. The personal care composition may exhibit a consumer preferred viscosity of greater than about 10,000 cps and less than about 50,000 cps. In other embodiments the viscosity is greater than about 30,000 cps or greater than about 40,000 cps. Viscosities are measured on a Brookfield viscometer using a T-C bar spindle with a heliopath setting at 5 rpm at 25° C. Typically, the personal care composition may comprise from about 0.1% to about 3% of the gelling agent. Percentages exceeding 3% are possible but have been found to exhibit undesirable characteristics (e.g., stringy skin feel).

The personal care compositions of the present invention comprise particulates such as platelet particulates or encapsulate particulates. Platelet particulates include pearlescent pigments, nacreous pigments, and interference pigments. Platelet particulates are known to exhibit a lustrous, iridescent, or angle-dependent optical effect. Platelet particles generally relate to particles wherein particle thickness is much smaller than the particle length and width. In certain embodiments, platelet particles have one axial dimension at least 5-times smaller than the other two axial dimensions. The personal care composition may comprise a visually perceptible amount of the platelet particulates. An "effective amount" means the minimal amount of platelet particulates to provide the personal care composition with a color or a pearlescent effect. In one embodiment, the personal care composition comprises from about 0.0001% to about 0.3% of the platelet particulates. While greater than 0.3% is clearly contemplated, platelet particulates in excess of about 0.1% may yield too opaque of a composition, which is not preferred by consumers. In suitable embodiments, platelet particles may have an average particle size of less than 100 microns.

Platelet particulates are typically heterogeneous materials. These platelets have a layered structure consisting of at least two optically different layer materials (e.g., pigments with layer-substrate structure or multilayer pigments without a substrate). Platelets can, for example, be made of natural or synthetic mica, silica, alumina, glass, boron nitride, and bismuth oxychloride. In suitable embodiments, the platelet particulates comprise mica. These platelets can be coated with one or more layers of other ingredients, such as metal oxides (e.g., tin oxide, titanium dioxide, iron oxides), silica, and organic materials such as various silicones, soaps, etc. These coating may exhibit optical properties different from the platelet material (e.g., titanium dioxide coated micas). In the case of interference pigments, the coating layer can be tailored (i.e., the refractive index of the coating and/or thickness of the coating) to yield a characteristic reflected color. Suitable interference pigments include micas comprising one or more layers of $TiO_2$, $Fe_2O_3$, silica, tin oxide, and/or $Cr_2O_3$ having a thickness of about 50 nm to about 300 nm thick. Interference pigments are available commercially from a wide variety of suppliers, for example, Presperse (Flonac™), Englehard (Duochrome™), Kobo (SK-45-R and SK-45-G), BASF (Sicopearls™), Eckart (Prestige™), and EMD Chemicals, Inc. (Colorona®, Timiron®, and Dichrona®).

Certain homogenous materials may also exhibit pearlescent, nacreous, or interference effects. Pigments without a layered structure include well-known metal effect pigments such as aluminum, copper, or copper-zinc alloy (bronze) platelets.

While platelet particulates are well known, inclusion of these particulates in a highly acid gel poses a unique problem. The platelet particulates are to be stably suspended such that the particulates do not settle during the normal lifespan of the personal care composition (e.g., from manufacture to final use), and the platelet particulates must be stably suspended such that the personal care composition does not cloud or become opaque.

In alternate embodiments, the present composition may comprise traditional high refractive index particulates that lack a pearlescent, nacreous, or interference effect such as iron oxides and titanium dioxide (in addition to or in lieu of the platelet particulates). High refractive index particulates have a refractive index greater than about 2.0.

In alternate embodiments, the present composition may comprise encapsulate particulates (in addition to or in lieu of the platelet particulates). Encapsulate particulates typically include a brittle or frangible material that may encapsulate another material that may be immiscible with the aqueous gel. However, the encapsulate particulate may be empty or may encapsulate a material that is miscible with the aqueous gel. U.S. Pat. No. 5,013,473 describes a suitable method for encapsulating oily materials for use in an aqueous cosmetic composition. U.S. Patent Application Publication No. US2006/0083761A1 describes a visible bead which may serve as a encapsulate particulate.

The personal care composition comprises a suspension agent capable of maintaining the platelet particulates in suspension during the normal lifespan of the personal care product. The suspension agents must not only suspend the platelet particulates but must also be pH tolerant and non-opacifying. For example, the suspension agent may be able to suspend the platelet particulates when initially formulated, but the acidity of the composition can degrade the suspension agent such that the platelet particulates settle out in time (i.e., generally within a week). Therefore, the suspension agent should be sufficiently robust to maintain the platelet particulates in suspension during the normal life span of the personal care product. Typically, the suspension should be maintained for at least about 8 weeks. Furthermore, the suspension agent should not cloud or opacify the personal care composition. Maintenance of a consumer preferred translucent gel is desired.

Suitable suspension agents include those materials listed as gelling agents. In one embodiment, the suspension agent is selected from xanthan gum, microfibrous cellulose, sodium carboxymethyl cellulose, and mixtures thereof. In a suitable embodiment, the suspension agent is a mixture of xanthan gum, microfibrous cellulose, and sodium carboxymethyl cellulose, which is commercially available as AxCel CG-PX from CP Kelco, San Diego, Calif. (having the CTFA designation of cellulose, xanthan gum, and cellulose gum).

The personal care composition may comprise an effective amount of the suspension agent to maintain the platelet particulates in suspension. In one embodiment, the personal care composition comprises at least about 0.01% of the suspension agent. The upper limit of the suspension agent is generally limited to maintain the consumer preferred transparency of the personal care composition and to provide adequate formulation space for other materials. In certain embodiments, the personal care composition may comprise from about 0.1% to about 0.4% of the suspension agent.

The personal care compositions of the present invention exhibit translucency. As used herein, "translucency" or "transparent" means that the composition exhibits a turbidity of less than about 900 NTU (Nephelometric Turbidity Units). In certain suitable embodiments, the personal care composition may exhibit a turbidity of less than about 700 NTU. The NTU values are measured using the VWR Scientific 66120-200 Turbidimeter calibrated with Formazin standards, available from VWR Scientific, West Chester, Pa. For purposes of the 66120-200 Turbidimeter, if the sample has a turbidity reading greater than 200 NTUs, the sample must be diluted and the turbidity calculated according to the following formula:

$$\frac{A \times (B + C)}{C} = D$$

A=NTU found in diluted samples
B=volume of deionized water used, mL
C=sample volume taken for dilution, mL
D=NTU of original, undiluted sample The dilution method is prescribed by and further detailed in the instructions accompanying the VWR Scientific 66120-200 Turbidimeter.

The personal care composition may be substantially free of oils. The term "substantially free of oils" means that the personal care composition comprises either no oils or that the personal care composition comprises a de minimus amount of oil that does not adversely impact the translucency (i.e., renders the composition non-translucent). It has been found that inclusion of oils in the personal care compositions can adversely affect the transparency of the composition.

Oils include silicone oils, hydrocarbon oils, fatty alcohols, fatty acids, esters of mono and dibasic carboxylic acids with mono and polyhydric alcohols, polyoxyethylenes, polyoxypropylenes, polyoxyethylene and/or polyoxypropylene ethers of fatty alcohols, polysiloxanes, paraffinic hydrocarbon oils, and mixtures thereof. Oils also include many organic sunscreen actives such as benzophenone-3, bis-ethylhexyloxyphenol methoxyphenyl triazine, butyl methoxydibenzoylmethane, diethylamino hydroxy-benzoyl hexyl benzoate, drometrizole trisiloxane, ethylhexyl methoxy-cinnamate, ethylhexyl salicylate, ethylhexyl triazone, octocrylene, homosalate, polysilicone-15, and derivatives and mixtures thereof. Oils also include oil soluble vitamins such as vitamin E (tocopherol and derivatives of tocopherol) and vitamin A (retinoids). Oils also include most commonly used perfumes and fragrances.

The personal care composition may further comprise one or more optional skin care actives. The personal care composition may include the optional skin care actives at levels that preserve the consumer preferred transparency and viscosity of the composition. In certain embodiments, the personal care composition may comprise from about 0.001% to about 20% of the skin care active.

Suitable skin care actives include, but are not limited to, vitamins, peptides, sugar amines, sunscreens, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobials, and antifungals. These skin care actives are provided in further detail in U.S. application publication No. US2006/0275237A1 and US2004/0175347A1.

Particularly suitable skin actives include vitamin B3 compounds, sugar amines, peptides, and hexamidine. As used herein, "vitamin $B_3$ compound" means a compound having the formula:

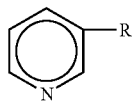

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. As used herein, "sugar amine" includes isomers and tautomers of such and its salts (e.g., HCl salt) and its derivatives. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). As used herein, "peptide" refers to peptides containing ten or fewer amino acids and their derivatives, isomers, and complexes with other species such as metal ions (e.g., copper, zinc, manganese, magnesium, and the like). The compositions of the present invention can include hexamidine compounds, its salts, and derivatives. As used herein, "hexaminide compound" means a compound having the formula:

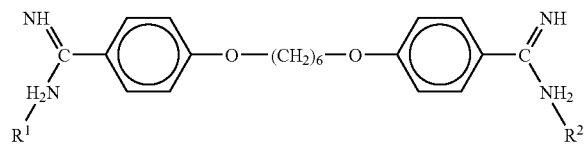

wherein $R^1$ and $R^2$ are optional or are organic acids (e.g., sulfonic acids, etc.).

The personal care compositions may be used to improve or regulate the condition of keratinous tissue. "Keratinous tissue" refers to keratin-containing layers disposed as the outermost protective covering of mammals which includes, but is not limited to, skin, hair, nails, cuticles, etc.

The personal care composition of the present invention may be applied to the skin at amount and frequency to regulate skin condition, to improve skin condition, to maintain or improve the signs of skin aging, or to maintain or improve insult-affected keratinous tissue. "To regulate skin condition" means maintaining skin appearance and/or feel with little to no degradation in appearance and/or feel. "To improve skin condition" means affecting a positive change in skin appearance and/or feel. The skin appearance and/or feel benefit may be a chronic benefit and may include one or more of the following: thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); preventing loss of skin or hair elasticity (e.g., due to loss, damage and/or inactivation of functional skin elastin, resulting in such conditions as elastosis, sagging, loss of skin or hair recoil from deformation); reduction in cellulite; change in coloration to the skin, hair, or nails, for example, under-eye circles, blotchiness (e.g., uneven red coloration due to, for example, rosacea), sallowness, and discoloration caused by hyperpigmentation.

"Signs of skin aging," include, but are not limited to, all outward visibly and tactilely perceptible manifestations, as well as any macro- or micro-effects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

"Insult-affected keratinous tissue," means keratinous tissue which exhibits discomfort, irritation, an unpleasant or irregular appearance, and the like, for example after exposure to a physical and/or chemical irritant. Non-limiting examples of insult-affected keratinous tissue include burn (e.g., sunburns, windburn, chemical or thermal burns); rashes (e.g., diaper rash, shaving rash and allergen-induced rashes); discoloration (e.g., bleaching, staining, hyperpigmentation); nicks and cuts (e.g., shaving insults); and dry, chapped or rough skin (e.g., due to exposure to example wind, cold and/or low humidity). Non-limiting examples of insults include radiation, wind, low humidity, allergens, pollutants, chemical and natural irritants, bodily fluids, bodily waste, excessive moisture, bacteria, fungi, etc.

In one aspect of the present invention, the personal care composition may be used to chemically exfoliate the skin. The personal care composition may be applied to the skin of a user prior to a primary sleep event. The personal care composition may be applied to the facial skin of a user. The primary sleep event is the longest period of rest in a 24 hour time period. Traditionally the primary sleep event is overnight bedrest. The primary sleep event typically lasts a minimum of 4-6 hours, but the time length is not particularly limited. Application of the personal care composition prior to the primary sleep event may occur within about 1 hour of the start of the primary sleep event. However, application of the personal care composition may be integrated into a routine most people have in preparation for the primary sleep event. The personal care composition remains on the skin of the user during the primary sleep event. The personal care composition may be removed from the skin of the user at the end of the primary sleep event. Typically, the composition may be removed from the skin when the user wakes in the morning after overnight bedrest. In one embodiment, the personal care composition may be removed from the skin by a water rinse.

Another aspect of the present invention relates to a method of marketing a personal care composition for chemical exfoliating the skin. The method may involve the step of providing the personal care composition as described above. The method further involves the step of proving instruction to a user to apply the composition prior to a primary sleep event of the user. The method further involves the step of providing instruction to the user to remove the personal care composition at the end of the primary sleep cycle.

EXAMPLES

Examples 8A-8D

The listed ingredients from water to d-panthenol are blended in a container. The gelling agent (A—Sepigel 305, B—Simulgel I-NS 100, C—Simulgel EG, or D—Sepiplus 600) and AxCel CDG-PX are added to the container and blended. The platelet particles are then added and blended.

| Example | 1 | 2 | 3 | 4 | 5 | 6 | 7 | 8A-D |
|---|---|---|---|---|---|---|---|---|
| Phase A | | | | | | | | |
| Water | QS (~20% total water) | QS (~20% total water) | QS (~20% total water) | QS (~20% total water) | QS (~20% total water) | QS (~20% total water) | QS (~20% total water) | QS |
| Glycerin | 10.0000 | 10.0000 | 10.0000 | 10.0000 | 10.0000 | 10.0000 | 10.0000 | 10.0000 |
| Allantoin | 0.1000 | 0.1000 | 0.1000 | 0.1000 | 0.1000 | 0.1000 | 0.1000 | 0.1000 |
| Sodium Ascorbyl Phosphate | 0.10000 | 0.10000 | 0.10000 | 0.10000 | 0.10000 | 0.10000 | 0.10000 | 0.10000 |
| Vitis Vinifera (Grapeseed) Extract | 0.02000 | 0.02000 | 0.02000 | 0.02000 | 0.02000 | 0.02000 | 0.02000 | 0.02000 |
| Green Tea Extract | 0.1 | 0.1 | 0.1 | 0.1 | 0.1 | 0.1 | 0.1 | 0.1 |
| Propylene Glycol | 1.0000 | 1.0000 | 1.0000 | 1.0000 | 1.0000 | 1.0000 | 1.0000 | 1.0000 |
| Butylene Glycol | 1.03950 | 1.03950 | 1.03950 | 1.03950 | 1.03950 | 1.03950 | 1.03950 | 1.03950 |
| Benzyl Alcohol | 0.4000 | 0.4000 | 0.4000 | 0.4000 | 0.4000 | 0.4000 | 0.4000 | 0.4000 |
| Matrixyl*[1] | 3.0 | 3.0 | 3.0 | 3.0 | 3.0 | 3.0 | 3.0 | 3.0 |
| Glycolic Acid | 3.9900 | 3.9900 | 3.9900 | 3.9900 | 3.9900 | 3.9900 | 3.9900 | 3.9900 |
| Triethanolamine | 1.0000 | 1.0000 | 1.0000 | 1.0000 | 1.0000 | 1.0000 | 1.0000 | 1.0000 |
| Sodium Hydroxide | 1.1250 | 1.1250 | 1.1250 | 1.1250 | 1.1250 | 1.1250 | 1.1250 | 1.1250 |
| Phase B | | | | | | | | |
| Water | QS (~80% total water) | QS (~80% total water) | QS (~80% total water) | QS (~80% total water) | QS (~80% total water) | QS (~80% total water) | QS (~80% total water) | — |
| d-Panthenol | 0.5000 | 0.5000 | 0.5000 | 0.5000 | 0.5000 | 0.5000 | 0.5000 | 0.5000 |
| Hydroxyethylcellulose | 1.00000 | 1.00000 | 1.00000 | 1.00000 | 1.00000 | 1.00000 | — | — |
| Ultrez 21*[2] | — | — | — | — | — | — | 1% | — |
| Sepigel 305*[3] | — | — | — | — | — | — | — | 3-5% A |
| Simulgel I-NS 100*[4] | — | — | — | — | — | — | — | 3-5% B |
| Simulgel EG*[5] | — | — | — | — | — | — | — | 3-5% C |
| Sepiplus 600*[6] | — | — | — | — | — | — | — | 3-5% D |
| AxCel CDG-PX*[7] | 0.10000 | 0.10000 | 0.10000 | — | 0.10000 | 0.10000 | 0.10000 | 0.10000 |
| After Mixing Phase A into Phase B, add: | | | | | | | | |
| Colorona Aborigne Amber*[8] | 0.02000 | 0.0001 | 0.3000 | 0.0200 | 0.1000 | 1.0000 | — | 0.0200 |
| Turbidity Value (NTU) | 117.8 | 102.2 | 870.0 | N/A | 620.0 | N/A | N/A | N/A |

*[1]Anti-aging peptide solution from Sederma, Inc., Edison, NJ.
*[2]Acrylates/C10-30 alkyl acrylate crosspolymer from Noveon Consumer Specialties, Cleveland, OH.
*[3]Polyacrylamide and C13-14 Isoparaffin and Laureth-7 from SEPPIC, Inc., Fairfield, NJ.
*[4]Hydroxyethyl acrylate/sodium acryloyldimethyl taurate copolymer and isohexadecane and polysorbate 60 from SEPPIC, Inc., Fairfield, NJ.
*[5]Sodium acrylate/sodium acryloyldimethyl taurate copolymer and isohexadecane and polysorbate 80 from SEPPIC, Inc., Fairfield, NJ.
*[6]Hydroxyethyl acrylate/sodium acryloyldimethyl taurate copolymer and isohexadecane and polysorbate 60 from SEPPIC, Inc., Fairfield, NJ.
*[7]Mixture of microfibrous cellulose, xanthan gum, and sodium carboxymethylcellulose from CP Kelco, San Diego, CA.
*[8]Mica coated with iron oxide, iron oxide black, and titanium dioxide from EMD Chemicals, Inc., Gibbstown, NJ.

Examples 1-6

Phase A materials are blended in a container. Phase B materials are blended in a separate container. Phase B is blended into Phase A. The platelet particulates are added after combining Phase A and Phase B.

Example 4 was unable to suspend the platelet particulates and falls outside of the present invention. Example 6 was visibly opaque and fails outside of the present invention.

Examples 7

Prepared similar to Examples 1-6. Viscosity could not be increased while maintaining suitable pH. Example 7 falls outside of the present invention.

These examples exhibited no translucency and no ability to suspend the platelet particles. Examples 8A-8D fall outside of the present invention.

Examples 1-3 and 5 are suitable for use according to the methods described above. Examples 1-3 and 5 may be applied to the skin at amount and frequency to regulate skin condition, to improve skin condition, to maintain or improve the signs of skin aging, or to maintain or improve insult-affected keratinous tissue.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition in the form of an aqueous gel comprising:
   a) about 0.1% to about 7.0% of glycolic acid, wherein the pH of the personal care composition is less than 4.5;
   b) about 0.1% to about 3% a gelling agent, wherein said gelling agent is hydroxyethyl cellulose;
   c) about 60% to about 95% of an aqueous solvent;
   d) from 0.0001% to about 0.3% of platelet particulates, wherein said platelet particulates comprise mica coated with metal oxide; and
   e) at least about 0.01% of a suspension agent to suspend the platelet particulates,
      wherein the suspension agent is a mixture of xanthan gum, microfibrous cellulose, and sodium carboxymethyl cellulose,
      wherein the personal care composition has a viscosity from about 10,000 cps to about 50,000 cps;
      wherein the personal care composition exhibits a turbidity of less than 900 NTU.

2. The personal care composition of claim 1 wherein the personal care composition comprises from about 1.0% to about 4% of glycolic acid.

3. The personal care composition of claim 1 wherein the pH of the personal care composition is from about 3.8 to about 4.2.

4. The personal care composition of claim 1 wherein the personal care composition is substantially free of oil.

5. The personal care composition of claim 1 further comprises an optional skin active selected from a group consisting of vitamins, peptides, sugar amines, sunscreens, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols, plant hormones, tyrosinase inhibitors, anti-inflammatory agents, N-acyl amino acid compounds, antimicrobials, and antifungals.

* * * * *